United States Patent [19]

Mallory et al.

[11] 4,321,466
[45] Mar. 23, 1982

[54] SENSITIVITY TEST SYSTEM FOR PHOTOELECTRIC SMOKE DETECTOR BY CHANGING LIGHT SOURCE INTENSITY

[75] Inventors: John Mallory; Zbignew W. Turlej, both of Toronto, Canada

[73] Assignee: Isotec Industries Limited, Toronto, Canada

[21] Appl. No.: 97,161

[22] Filed: Nov. 26, 1979

[51] Int. Cl.³ .............................................. G01N 15/06
[52] U.S. Cl. ..................................... 250/574; 340/630
[58] Field of Search ...................... 250/573, 574, 575; 340/630; 356/338-343

[56] References Cited

U.S. PATENT DOCUMENTS

| | | | |
|---|---|---|---|
| 3,376,425 | 4/1968 | Kraus et al. | 250/573 |
| 3,510,666 | 5/1970 | Topol | 250/574 |
| 3,655,289 | 4/1972 | Walker | 250/574 |
| 3,812,482 | 5/1974 | Clark | 250/573 |
| 3,935,876 | 2/1976 | Massie et al. | 250/574 |
| 4,099,178 | 7/1978 | Ranney et al. | 340/630 |

*Primary Examiner*—David C. Nelms

[57] ABSTRACT

A tester device is disclosed for a photoelectric smoke detector. The tester, when actuated, increases the intensity of light emitted by a light source to simulate in the sample chamber by such light scattering and reflecting off chamber walls, an amount of light which would be scattered by a predetermined concentration of smoke to which a photoelectric sensor is responsive and causes an indication that the detector is functioning as intended.

15 Claims, 3 Drawing Figures

SENSITIVITY TEST SYSTEM FOR PHOTOELECTRIC SMOKE DETECTOR BY CHANGING LIGHT SOURCE INTENSITY

FIELD OF THE INVENTION

This invention relates to testing systems for photoelectric smoke detectors.

BACKGROUND OF THE INVENTION

Photoelectric smoke detectors are commonly used to detect the presence of smoke particles in the air by sensing the scattering of light energy by smoke particles in a sample chamber of the detector. The sample chamber is commonly made with walls which have a dull black finish to minimize light reflection. A source of light is positioned to shine a beam of light into the chamber. Should there be smoke present in the chamber, the beam of light energy is scattered by the smoke particles and a portion of such scattered light is sensed by photoelectric sensor, such as, a photodiode or the like, to cause an alarm upon sensing an amount of scattered light energy which results from a predetermined smoke concentration.

One of the concerns in using a photoelectric smoke detector is that the photoelectric sensor and the source of light, such as a light emitting diode and associated electronic circuitry, are prone to failure or change in characteristics over extended periods. It is, therefore, important to provide on the detector a type of test unit that, when actuated by the consumer, indicates the device is still functioning as intended.

Several approaches have been taken in the past to provide test units for photoelectric smoke detectors, such as that disclosed in U.S. Pat. No. 3,868,184. This patent discloses a particle simulating device for testing the operativeness of the photoelectric sensing cell and its associated alarm circuit. The particle simulating device comprises a thin wire mounted on a bell crank which is manually operated from outside of the detector to swing the wire through the detection zone at the intersection of lamp and photocell axis, so as to scatter light from lamp to the cell in the same way an amount of particles in the zone would accomplish. This arrangement lacks precision in simulating a predetermined smoke concentration, since it is very difficult to mount in the detector a sufficiently thin wire to simulate a light scattering which would be caused by a concentration of smoke in the range of 1.5 to 3% obscuration.

In an attempt to improve the precision of the mechanical device for simulating predetermined concentrations of smoke, a wire may be positioned to swing into the sensitive area of the chamber, which is not at the intersection of the lamp and photocell axis. This permits the use of a larger diameter wire to scatter light which has strayed from the light beam. The difficulty with this arrangement is that a very exact location is needed in positioning the wire in the sensitive zone to provide a consistent scattering of an amount of light. This entails the use of a complex mechanical linkage which will always ensure the exact positioning for the wire in the sensitive zone and must be such that the swinging movement of the wire is always the same and is not directly dependent upon the extent to which a test button is pressed by the consumer.

Another approach for testing photoelectric smoke detectors is disclosed in U.S. Pat. No. 4,099,178. In that instance, the test means includes a light source and light responsive device and has a separate test light path other than through the smoke chamber with light modifying means in the test path to simulate a preselected smoke density. The test means includes a normally closed gate for the test light path, the gate being manually opened to transmit light along the test path to the light responsive device to cause actuation of the alarm in the absence of smoke to indicate detector operability. This arrangement entails the incorporation into the device of a separate test light path other than the normal path and the use of a mechanical linkage or the like to provide externally of the device means for opening and closing of the gate which permits the light from the light source to travel along the test light path. The selection of the light modifying means in the test path is critical, because with variations in its characteristics, there is a result in variation in the sensitivity at which the detector is tested. Thus, to ensure a testing of the device in a desired sensitivity range, it is important to have rigid standards which must be met by the light modifying means, such as opaque tape, to maintain a test in desired sensitivity range.

With the above form of testing devices for smoke detectors, there is little, if any, flexibility in adjusting for changes in the characteristics of the detector components. This may arise, for example, in changing sources of supply for the photoelectric sensor, the light source or other electronic components. With mechanical devices for providing light scattering adjustment of the amount of light to be scattered is very difficult, if not impossible, with most units. Therefore, once the particular size and location of the mechanical test unit has been determined, it is important to continue with the same source of supply of the components to ensure that the manufactured units are tested at the same sensitivity.

SUMMARY OF THE INVENTION

The test arrangement, according to this invention, overcomes the above problems in a simple manner, yet provides a reasonably accurate testing of the detector sensitivity and operativeness over the life of the unit.

The test arrangement may be incorporated in a photoelectric smoke detector of the type having a smoke chamber, a light source and a photoelectric sensor responsive to light scattered by smoke in the chamber to cause an alarm at a predetermined concentration of smoke. The test means, when actuated, is adapted to increase light intensity from the light source to a level which simulates in an essentially smoke-free chamber an amount of light scattered and reflected by chamber walls onto the sensor equivalent to that which would be scattered by at least the said predetermined concentration of smoke. The level of increased light intensity causes a device to indicate to the person testing the unit that the detector is operable and is responding at a desired sensitivity.

Thus, the method according to this invention for testing the sensitivity of a photoelectric smoke detector, comprises increasing the light intensity of the smoke detector light source to a level which simulates in an essentially smoke-free chamber a sensed amount of light energy scattered and reflected onto the sensor by chamber walls, which is equivalent to that which would be scattered by at least the predetermined concentration of smoke.

DESCRIPTION OF THE DRAWINGS

Preferred embodiments of the invention are shown in the drawings wherein.

DETAILED DESCRIPTION OF THE PREFERRED EMBODIMENTS

Photoelectric smoke detectors may be used in commercial, industrial or residential establishments for detecting smoke. The detector may be battery powered or powered by a constant voltage supply which may be AC converted into DC voltage. It may be desirable in some instances to combine the use of a photoelectric smoke detector with a dual ionization chamber type of smoke detector to ensure that most forms of smoke particles, caused by various types of fires, are sensed.

It is understood that the term light to describe the energy emitted by the light source includes all radiant energy which is capable of being scattered by smoke particles in a sample chamber. Such radiant energy may be in the range of infrared, visible and some of the ultraviolet region. The use of the infrared or ultraviolet radiation, as emitted by the light source, has the distinct advantage, because the photoelectric sensor may be tuned to be sensitive to only energy in the infrared or ultraviolet range to reduce the effect external visible light has on the detector.

Figure 1:
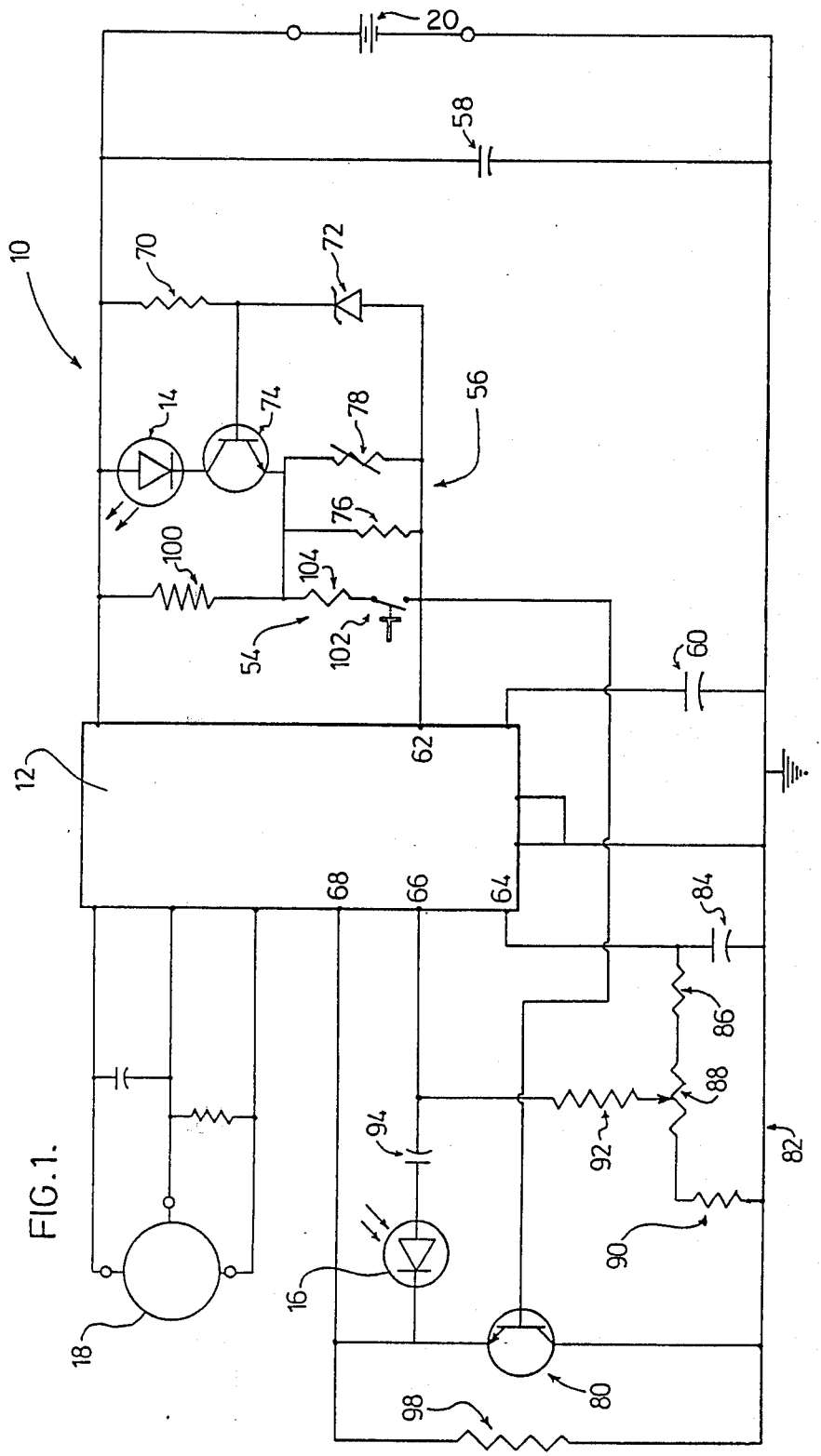
FIG. 1 is a schematic representation of a preferred type of electronic circuitry for a battery powered photoelectric smoke detector having test means.

FIG. 1 of the drawings shows a representative electronic circuit for use in association with a photoelectric smoke detector having test means according to this invention. The circuitry generally designated 10 comprises an integrated circuit chip 12 which acts as the controller for the circuit. It periodically activates the light source 14 and, upon sensing scattered light by a light sensor 16 caused by the presence of smoke particles, it sounds an alarm such as an audible piezo-electric alarm 18. In this embodiment, the integrated circuit and related components are powered by a nine volt battery 20.

Figure 2:
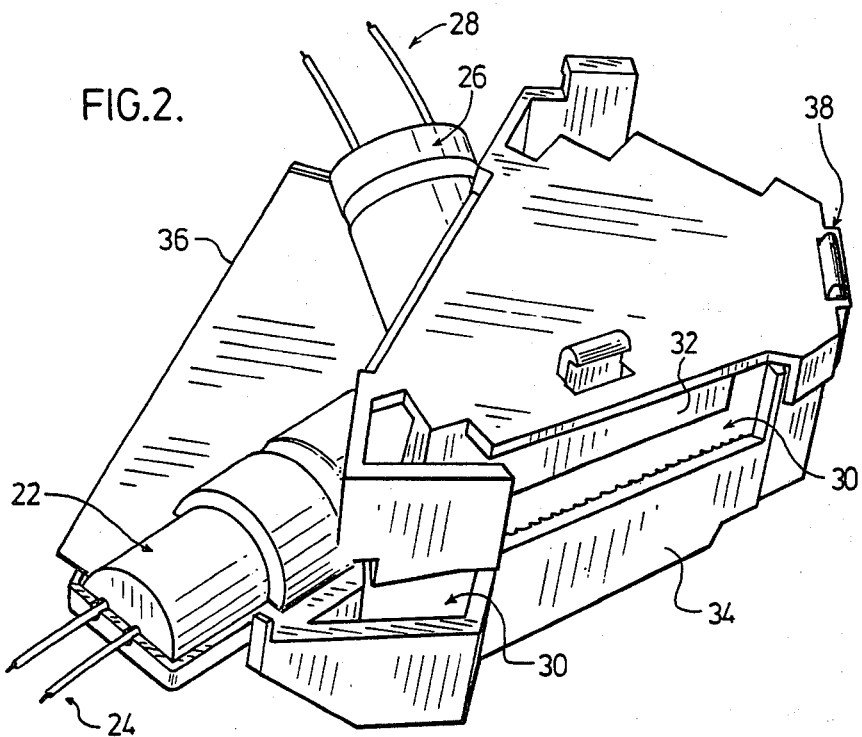
FIG. 2 is a preferred embodiment for the sample chamber of the photoelectric detector.

As shown in FIG. 2, a preferred arrangement for a smoke detector chamber is shown where the light source is housed in chamber barrel portion 22 with leads 24 extending outwardly therefrom and which are part of the circuit of FIG. 1. Correspondingly, the photoelectric sensor is housed in chamber barrel portion 26 and has leads 28 which form part of the circuitry. The chamber is provided with a plurality of openings 30 which permit smoke in the air to enter the chamber. Various forms of light blocking devices are found about the openings, such as baffle 32 which, if the chamber is looked at from a horizontal attitude, overlaps outer wall 34 to prevent light from entering the chamber directly through the opening 30. Other forms of baffling arrangements are located about the other openings to minimize, if not essentially eliminate, the amount of outside light which may enter the chamber.

Preferably the chamber may be formed from injection molded plastic and made in two parts hinged about area 36. The two parts may be closed together and clipped shut by clip 38.

Figure 3:
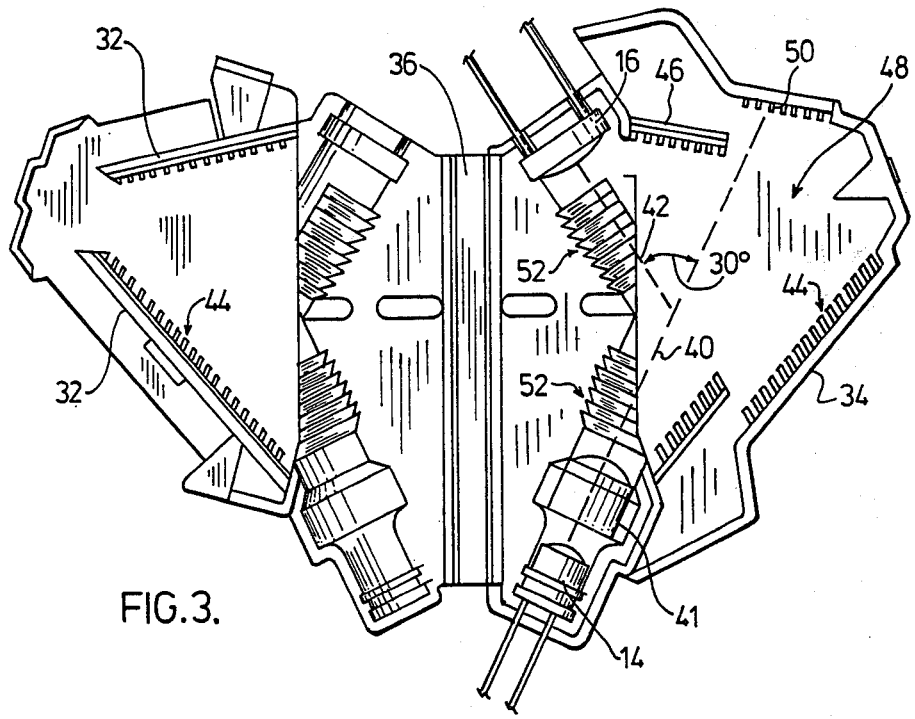
FIG. 3 shows the sample chamber of FIG. 2 opened about its hinged axis to show the interior configuration thereof.

Further details of the interior of the sample chamber are shown in FIG. 3 where the chamber parts lay open. The beam of light 40 from source 14, focused by lens 41, is directed along the path shown in dotted line. Should there be smoke in the chamber, a portion of light energy scattered by smoke particles impinges on sensor 16 along the path 42 shown in dot. By computer analysis, it has been found that, to provide an acceptable degree of light scattering by smoke particles, the minimum chamber size should have an optical depth of approximately 2 to 3 centimeters. An optimum positioning of the sensor 16, relative to the light source 14 for sensing the amounts of light energy scattered by smoke particles, is 30° away from the light beam, as shown in the drawing.

The chamber walls, such as wall 34, have on its inside surface a plurality of vanes or flutes 44 which serve to minimize the reflectivity of the surface and cause some scattering of impinging light. The reflectivity is further reduced by providing a dull black finish on the inside of the chamber walls. Various numbers and positioning of baffles, such as 46, are located about the interior of the chamber to provide blocking for light entering through the openings 30 to the chamber. Thus, when there is little, if any, smoke particles or other particles in the sample chamber, generally designated 48, light emitted from the light source 14 will follow path 40 and partially be absorbed by wall 50 and remaining energy is reflected and scattered from that portion of the wall onto other walls in the chamber where most of the remaining light energy is absorbed. A very small amount of light energy is, however, scattered onto the sensor 16 which is insufficient to cause an alarm. The shaping of the barrels 22 and 26 for the light source and sensor include a plurality of vanes 52, which are shaped to absorb any stray light from emitted beam 40 and to absorb any stray light travelling down barrel 26 along path 42 towards the sensor 16. In this embodiment, it is accomplished by sloping the surfaces of the vanes to essentially trap and reflect or scatter backwards some of the light energy, and due to the dull black finish, absorb most of the remaining tray light energy.

There are several types of electronic circuits which may be used in operating photoelectric smoke detectors, thus the one shown in FIG. 1 is illustrated to exemplify a preferred type of circuitry. Depending upon the conditions for smoke detection, it may desirable to work in a range which is outside the visible region to reduce the effect that ambient visible light may have on the detector. Thus, the light source 14 may be a light emitting diode which has the characteristics, when powered, to emit radiant energy in the infrared range, which may be in the area of 900 nanometers. Thus, the photoelectric sensor 16 may be a photodiode which is tuned to sense principally radiant energy in the corresponding range of 900 nanometers. It is, of course, appreciated that the system may be operated in the visible or ultraviolet range and that other than light emitting diodes may be used with the photoelectric sensor tuned accordingly. It is essential, however, that the chosen wavelength for the radiant energy be such that it will be effectively scattered by smoke particles which may enter the chamber 48 of the detector.

Aside from the standard arrangement for the circuitry 10 for the smoke detector, the circuitry includes a test device which, when actuated, determines the operability of the circuit and if it is reacting at a desired sensitivity.

Electronically, various techniques may be employed to cause an increase in light intensity upon actuation of the test means; one of which is exemplified by the following preferred embodiment.

The tester arrangement is generally designated 54 and forms part of the resistor network generally designated 56. The tester works on the principle of increasing the level of light or radiant energy intensity emitted by the light source 14 to provide an amount of energy scattered and reflected by the interior surfaces of the chamber 48, which impinges upon light sensor 16 to simulate the same amount of energy which would be scattered by a predetermined concentration of smoke particles. The increased level of light intensity may, therefore, be determined in simulating a desired smoke concentration to thus either actuate the alarm 18 or some other device to indicate detector operability and that it is sensitive at a desired level.

To further assist in the understanding of the test means operation, reference is made to the details of the detector circuitry. The integrated circuit chip 12, as the controller implements the functions of timing, creation of a stable voltage reference, voltage level detection and control of a solid state piezo-electric alarm. The circuit is powered by a single nine volt battery 20 which, in normal operation, has an expected life in excess of one year. The circuit 10 is designed so that it will continue to operate accurately even as the battery discharges with use over time and cannot maintain its full specified voltage under load conditions. Connected in parallel with the battery is a suitably large capacitor 58 which reduces fluctuation in the voltage delivered to the circuit as rapidly varying current demands are imposed by the circuit. A capacitor 60 controls the internal timing circuitry of the chip 12. The circuitry of chip 12 periodically pulls pin 62 from a floating high voltage state (hereinafter referred to as "off") to a near ground state (hereinafter referred to as "on") for a short time duration according to this embodiment of approximately 200 microseconds.

The chip 12 produces a very accurate reference voltage level at pin 64, which is independent of the supply voltage and which forms part of establishing a reference in adjusting the sensitivity of the photodiode 16.

A voltage level detection circuit on the chip triggers the piezo-electric alarm when the voltage difference across pins 66, 68 drops below a certain critical level.

When pin 62 is "on," current flows from the positive terminal of the battery through resistor 70 and the zener diode 72 to pin 62 which is near ground. A well defined voltage independent of the power supply is established on the base of transistor 74 and, therefore, a well defined voltage is established at the emitter of transistor 74. Resistor 76 of the resistor network is in parallel with a thermistor 78. As is appreciated, the thermistor 78 compensates for changes in the characteristics of the photo-sensitive diode 16 due to fluctuations in temperature. Resistors 76,78 allow a well defined and thus temperature compensated current to flow through the emitter of transistor 74. A current independent of the power supply voltage passes through the collector of transistor 74 and light emitting diode 15 to illuminate same at a well defined level of radiant energy which may, as explained, be in the range of 900 nanometers.

Transistor 80, as associated with the photodetection side of the circuitry, is inactive when pin 62 is near ground and its "on" state, because the base of the transistor will also be near ground. The voltage dividing network generally designated 82 which consists of parallel connection of capacitor 84 with series connection of the resistor 86, potentiometer 88 and resistor 90, is connected from the well established reference voltage at pin 64 on the chip to ground. An adjustable yet stable voltage is produced at the wiper contact of potentiometer 88. This voltage is fed to pin 66 of the voltage level detection circuit on the chip through a resistor 92. Pin 66 is connected through a circuit decoupling capacitor 94 to the anode of photodiode 16. The cathode of the photodiode 16 is connected to pin 68 of the voltage level detection circuit in the chip and through resistor 98 to ground. The voltage dividing network 86 is thus provided with the voltage established at the wiper contact of potentiometer 88. An amount of radiant energy scattered by smoke in the chamber impinges upon the photodiode 16 and causes the resistance of the photodiode to decrease to a point such that the voltage across pins 66, 68 of the voltage detection circuit on the chip will drop below the critical level and the alarm 18 will be triggered.

In factory calibration of a production unit, the detector is placed in a controlled and clean environment. Potentiometer 88 is adjusted to the point where the alarm 18 begins sounding when light emitting diode 14 is illuminated. By experiment, it has been determined for the particular parameters of this circuit that the wiper contact voltage of the potentiometer 88 can be increased a determined amount; namely 2 millivolts, to give the desired detector sensitivity. The device, when subsequently used in an environment, will sound an alarm for a desired smoke sensitivity of concentration equal to approximately 1.5% obscuration.

When pin 62 on the chip is "off," which is the large percentage of the time, transistor 74 is inactive and LED 14 is not illuminated. A small current flows from the positive terminal of the battery 20 through the series connection of resistor 100, the parallel connection of resistor 76 and thermistor 78 to the base of the transistor 80. Since the collector of transistor 80 is at ground, transistor 80 enters a mode in which the effective resistance across its collector and emitter is very low. The emitter of transistor 80 is pulled to approximately ground. This ensures that, when pin 9 on the chip is "off," any extraneous transient current from the cathode of the photodiode 16 will be shunted to ground. This arrangement, therefore, avoids erroneous triggering of the alarm because the voltage at pin 68 of the voltage level detection circuit cannot rise.

The testing device 54, according to the shown embodiment, has a manually operated switch 102 which is normally open. This switch may be closed to test for the operation and sensitivity of the detector circuit. When the switch 102 is closed, resistor 104 is connected in parallel with resistor 76 and thermistor 78 to provide additional current through the LED 14 when pin 62 on the chip is "on." Resistor 104 has a value which has been established by experiment for the particular circuit parameters to increase the current flowing through the light emitting diode 14 to a value which causes the LED to increase the level of light intensity. The level of increased radiant energy is such as to provide an amount of energy scattered and reflected off the walls impinging upon the photodiode 16, assuming the chamber to be essentially clear of smoke, to simulate an amount of light which would be scattered by a smoke obscuration of 3%. Pushing test button 102, assuming the circuitry to be operative, causes the alarm 18 to sound so that the person testing the device is assured that the circuit is operational and sensitive to at least 3% smoke obscuration and it would respond in normal operation to an environmental obscuration of approximately 3% or more. At the time of testing, should there be a concentration of smoke in the chamber which is less than that needed normally to set off an alarm, the amount of scattered and reflected light impinging on the sensor, when the test button is pushed, will be greater than the desired sensitivity test level of 3%. Other background noise may appear in the form of the previously explained very small amount of light directed onto the sensor by chamber walls. This is not considered a problem, because such background noise is usually at a relatively low value. It is appreciated that a lesser percentage obscuration may be tested for in terms of detector sensitivity by simply chosing another value for resistor 104 to produce a lower level of increased light intensity which would simulate, for example, 1.5% smoke obscuration.

This manner of testing the photoelectric smoke detector avoids the need for any complicated mechanical linkage for swinging into the sensitive region of the chamber a light scattering device. The complete testing operation is accomplished electronically where the integrity of both the integrated circuitry and the light source and light sensor are tested. Any desired sensitivity of the device greater than that for which the device is set for, can also be established by way of making appropriate alterations to the resistor network 56.

Aside from the calibration adjustments provided by voltage divider network 82 for the photo-sensitive diode 16, a calibration adjustment may also be provided for the light emitting diode 14. This may be accomplished by substituting for fixed resistor 104 a potentiometer. After calibration of the photosensitive diode 16 in the manner previously discussed, it may also be determined by experimentation that, to compensate for a change in the characteristics of the light emitting diode 14 or change in chamber characteristics, the potentiometer in place of fixed resistor 104 may be varied to provide the needed voltage pulse height through photoelectric diode 16 which would be the same as that caused by a smoke obscuration of desired concentration. Thus, by providing an electronic form of testing the detector, there is the added advantage of providing a unit which can compensate for variations in the characteristics of the photoelectric diode, light emitting diode and other characteristics of the circuitry. As a result, it is not necessary to maintain rigid controls on the characteristics of components and thus permit obtaining components for the detector from several different sources of supply. This appreciably facilitates manufacture of the unit and, by reducing the rigid standards on component characteristics, also reduces the cost of manufacture of the unit.

In the illustrated embodiment, switch 102 is incorporated on the device itself and is simply a mechanical switch. However, a remote means of testing the circuit integrity can be accomplished by a relay mechanism or other suitable means. It is also possible to automatically test the circuit sensitivity by increasing the complexity of the chip to periodically switch in resistor 104. The sounding of the alarm would be suppressed and would only be sounded if the circuit did not detect the simulated increased obscuration by increasing the level of light intensity from light emitting diode 14.

In operation of the unit, should the device detect a smoke obscuration of 1.5% or more, the alarm will sound. The system then checks for smoke obscuration every five seconds after the first detection, where the alarm is resounded after the first five second interval, should the smoke remain in the chamber. This recheck on the presence of smoke is continued until the smoke leaves the chamber.

The integrated circuit chip 12 may also include battery voltage sensing device which will actuate an alarm or some other indication means to let the consumer know when the battery has achieved its low battery setting, which in this instance, is considered to be 7.5 volts. At that time, the battery should be replaced to maintain proper operation of the circuitry.

It is also appreciated that, in actuating the test device 54 for determining detector operability, a device other than the alarm 18 may be actuated to indicate circuit integrity. Such a device may be a light or some other system of indication. In particular when the unit is tested from a remote central control panel, an appropriate light may be employed to indicate circuitry operativeness.

Although various embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. In a photoelectric smoke detector for setting off an alarm on detecting a predetermined concentration of smoke particles in the air, said detector having an open chamber into which smoke particles may enter, a source of radiant energy being directed along a path through said chamber and which is capable of being scattered by smoke particles in said chamber and being scattered and reflected by wall portions of said chamber, a photoelectric sensor offset from said path of radiant energy for sensing scattered radiant energy, a controller connected to said sensor and adapted to actuate an alarm when said sensor senses an amount of radiant energy scattered by said predetermined concentration of smoke particles in said chamber, said chamber wall portions being adapted to scatter and reflect a relatively small portion of incident radiant energy from said source which is insufficient to actuate said alarm, test means for testing said detector, said test means when actuated, being adapted to increase the level of radiant energy emitted by said source to a level which produces an amount of radiant energy scattered and reflected by said wall portions of said chamber essentially free of smoke particles onto said sensor to simulate that which would be scattered by a concentration of smoke particles essentially the same as said predetermined concentration and thereby actuate a device to confirm detector operability and desired sensitivity.

2. In a photoelectric smoke detector of claim 1, said source of radiant energy emitting infrared radiation to which said photoelectric sensor is sensitive.

3. In a photoelectric smoke detector of claim 1, said source of infrared radiation being a light emitting diode which emits infrared radiation in the range of 900 nanometers, said photoelectric sensor being tuned to be sensitive to infrared radiation of similar wavelength.

4. In a photoelectric smoke detector of claim 1, said source of radiant energy being pulsed.

5. In a photoelectric smoke detector of claim 4, a pulse of radiant energy being emitted every ten seconds for a duration of 200 microseconds.

6. In a photoelectric smoke detector of claim 1, said photoelectric sensor being located to sense scattered radiation impinging on said sensor along a path which is at an angle of approximately 30° from the path of the emitted radiant energy.

7. In a photoelectric smoke detector of claim 1, the electrical circuitry being battery powered.

8. In a photoelectric smoke detector of claim 1, said chamber walls having a dull black finish to provide a low level of light reflectivity.

9. In a photoelectric smoke detector of claim 8, said chamber walls being irregular.

10. In a photoelectric smoke detector of claim 1, said source of radiant energy being an electrically powered light emitting diode where said test means, when actuated, increases current through said light emitting diode to give the desired level of increased radiant energy intensity.

11. In a photoelectric smoke detector of claim 10, a resistance network in series with said light emitting diode, said resistance network comprising a first resistor means, a second resistor means in parallel with said first resistor means, said test means, when actuated, including said second resistor means in said network to thereby decrease the overall resistance of said network, the resistance values of said first and second resistor means being selected to cause a greater current through said light emitting diode to provide said level of increased light intensity.

12. In a photoelectric smoke detector of claim 11, a pushbutton exteriorly accessible of said detector, said button when pushed closing a normally open switch to include said second resistor means in said resistor network.

13. In a photoelectric smoke detector of claim 1, said detector being calibrated to cause an alarm for a smoke concentration of 1.5% obscuration, said tester increasing light intensity to a level to simulate an amount of light scattered by a smoke concentration of 3% obscuration or less for a chamber essentially free of smoke particles.

14. In a photoelectric smoke detector of claim 1, said device to confirm operability being said alarm which sounds a short alarm to indicate desired detector sensitivity.

15. In a photoelectric smoke detector of claim 11, said second resistor means being a variable resistor arrangement to provide adjustable resistance values for said second resistor means.

* * * * *